(12) United States Patent
Radomski et al.

(10) Patent No.: US 7,992,554 B2
(45) Date of Patent: Aug. 9, 2011

(54) LIQUID EVAPORATOR

(75) Inventors: Klaus Radomski, Luebeck (DE);
Norbert Wruck, Luebeck (DE); Jochim Koch, Ratzeburg (DE)

(73) Assignee: Dräger Medical GmbH, Lübeck (DE)

( * ) Notice: Subject to any disclaimer, the term of this patent is extended or adjusted under 35 U.S.C. 154(b) by 1321 days.

(21) Appl. No.: 11/537,756

(22) Filed: Oct. 2, 2006

(65) Prior Publication Data
US 2007/0107879 A1 May 17, 2007

(30) Foreign Application Priority Data

Nov. 15, 2005 (DE) .......................... 10 2005 054 344

(51) Int. Cl.
*A61M 15/00* (2006.01)
*A61M 16/00* (2006.01)
*A01G 13/06* (2006.01)
*A61H 33/06* (2006.01)
*F24F 6/08* (2006.01)
*F24F 3/14* (2006.01)
*C10B 29/00* (2006.01)

(52) U.S. Cl. ......... 128/204.17; 128/203.26; 128/203.27; 128/203.12; 128/203.16; 128/203.17; 128/204.14; 128/204.13; 128/203.25; 128/204.18; 392/386; 392/394; 392/395; 236/44 A; 236/44 B; 159/906; 159/DIG. 15; 159/DIG. 27; 159/DIG. 28; 202/267

(58) Field of Classification Search ............. 128/203.26, 128/203.27, 203.12, 203.16, 203.17, 204.14, 128/204.13, 204.17, 203.25, 204.18, 213.13; 392/386, 394, 395; 236/44 A, 44 C; 159/906, 159/DIG. 15, DIG. 27, DIG. 28; 202/267
See application file for complete search history.

(56) References Cited

U.S. PATENT DOCUMENTS
7,694,675 B2 * 4/2010 Koch et al. ............... 128/203.17

FOREIGN PATENT DOCUMENTS
DE 19808590 C2 9/1999
* cited by examiner

*Primary Examiner* — Patricia M Bianco
*Assistant Examiner* — Nihir Patel
(74) *Attorney, Agent, or Firm* — McGlew and Tuttle, P.C.

(57) ABSTRACT

A liquid evaporator includes a liquid reservoir (3) with a liquid to be evaporated, a heater (9) and an evaporator tube (12). The evaporator tube (12) has a first porous element (1) having a first porosity and with an area in contact with the liquid in the liquid reservoir (3) and a second porous element (2) with a second porosity and with an area present on an evaporator side (50) used to dispense the evaporated liquid, and an area outside the liquid reservoir heated by the heater (9) which is not directly in connection with the liquid. The first porous element and the second porous element are in contact in contact areas with the first porous element forming a wick delivering liquid from the reservoir to the contact area.

24 Claims, 4 Drawing Sheets

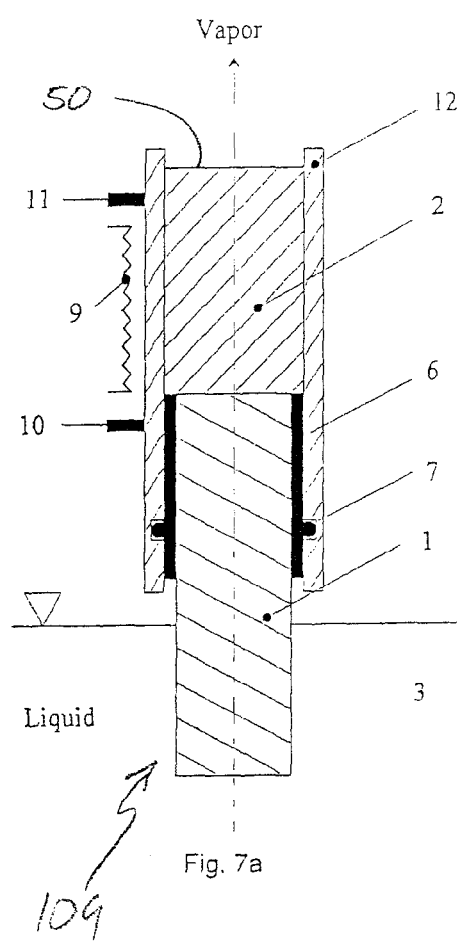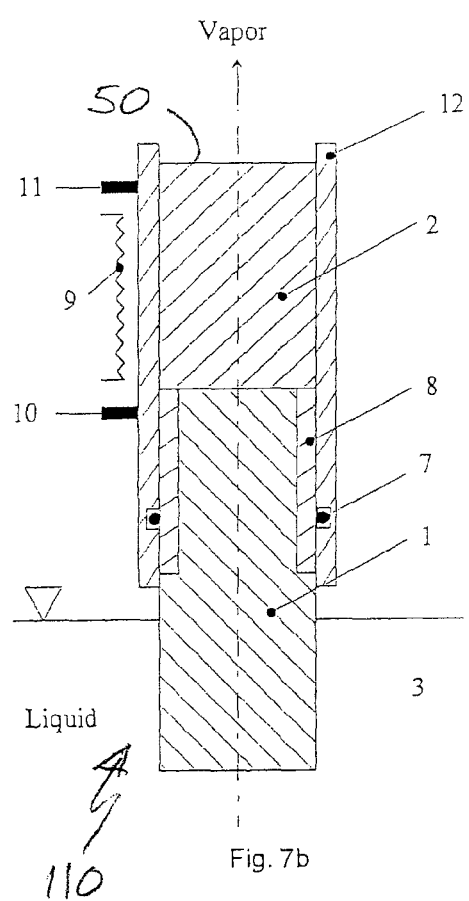

LIQUID EVAPORATOR

CROSS REFERENCE TO RELATED APPLICATIONS

This application claims the benefit of priority under 35 U.S.C.§119 of German Patent Application DE 10 2005 054 344.8 filed Nov. 15, 2005 the entire contents of which are incorporated herein by reference.

FIELD OF THE INVENTION

The present invention pertains to a liquid evaporator, which is used to dispense an anesthetic or as a breathing gas humidifier for a patient.

BACKGROUND OF THE INVENTION

The breathing gas humidifiers used hitherto have, in general, active humidifying systems with heated evaporator chambers, over which the breathing gas to be humidified is sent. These humidifiers have high resistance and high compliance, which has a disturbing effect on the quality of artificial respiration. In addition, these humidifying systems have a relatively long heat-up time because the humidifier must first heat up the total amount of water present in the evaporator chamber before the humidifier can reach the desired humidification capacity. This may take up to 30 minutes, and the humidification capacity is reduced relatively greatly each time cold water is added, which is disadvantageous for the respiration therapy.

Mechanical dispensing units, such as pumps and valves, are also used during the evaporation of volatile anesthetics. It is disadvantageous in this connection that the mechanical components must be replaced after a certain time because of wear. The actorics components must be made of materials that are resistant to anesthetics, which causes high costs.

A known humidifier became known from DE 198 08 590 C2, in which the dispensing of the quantity of water, which depends on the respiratory volume flow, with superheated water vapor is described. The drawback of this arrangement is the necessary pump to dispense the quantity of water. Thus, there are parts subject to wear, which must be regularly replaced by the user.

SUMMARY OF THE INVENTION

Accordingly, the object of the present invention is to improve a liquid evaporator, so that its design is further simplified and, in particular, no pump is needed for its operation any longer.

According to the invention, a liquid evaporator is provided with a liquid reservoir with a liquid to be evaporated. An evaporator tube is provided which is heated by means of a heater and which is provided with adjacent areas consisting of materials of different porosities. The one or more areas include one or more of porous sintered glass or porous sintered ceramic elements, which areas are in connection with the liquid in the liquid reservoir and are present on one front side of the liquid evaporator. The other front side is used to dispense the evaporated liquid. An area of the evaporator tube outside the liquid reservoir, which area is heated by means of the heater is provided with a porous sintered metal or porous sintered ceramic, which is not directly in connection with the liquid. At least two different cross section distributions of the materials having different porosities are present in the longitudinal direction of the liquid evaporator. The areas in the liquid evaporator are adjacently in connection by means of three-dimensionally shaped contact areas.

According to another aspect of the invention, a liquid evaporator is provided with a liquid reservoir with a liquid to be evaporated. An evaporator tube is heated by means of a heater and is equipped with adjacent areas consisting of materials having different porosities. One or more areas have one or more porous sintered glass or porous sintered ceramic elements which areas are in connection with the liquid in the liquid reservoir, present on one front side of the liquid evaporator. The other front side is used to dispense the evaporated liquid. An area of the evaporator tube outside the liquid reservoir, which area is heated by means of the heater is equipped with a porous sintered metal or porous sintered ceramic, which is not directly in connection with the liquid. At least two different cross section distributions of the materials having different porosities are present in the longitudinal direction of the liquid evaporator. The area or areas of the liquid evaporator that are in connection with the liquid are equipped with a gas-tight jacket or are inserted into the evaporator tube such that the liquid cannot escape from the evaporator tube to the outside against the direction of dispensing when a respiration pressure is present on the front side for dispensing the evaporated liquid.

The liquid evaporator according to the invention advantageously may have no mobile parts. The liquid to be evaporated is delivered into the evaporator tube by capillary forces. The capillary pump consists of a porous material, especially sintered glass or sintered ceramic ($Al_2O_3$), which is in connection with the liquid to be evaporated. To guarantee the back pressure independence of the respiration side following in the downstream direction, the section acting as a capillary wick must be provided with relatively fine pores withstand a respiration pressure of 100 mbar, it is possible, for example, to use sintered elements with a porosity of P16 according to ISO 4793 with a mean pore diameter of 10 μm to 16 μm for the section acting as a capillary wick if water is used as the liquid to be evaporated. The increase in the contact areas between the section acting as a capillary wick and the evaporator tube, which is heated from the outside and consists of a sintered metal or a porous sintered ceramic with a porosity of, for example, P100 with a mean pore diameter of 40 μm to 100 μm, is achieved especially by extending the section acting as a capillary wick into the evaporator section, for example, in a conical shape. The energy of evaporation is thus transmitted not only from the upper section of the liquid evaporator, but also through the lateral or jacket surface to the section acting as a capillary wick, so that the evaporation capacity is substantially increased. A gas-tight jacket in the upper area of the section of the liquid evaporator, which section acts as a capillary wick, optionally ensures good sealing against the environment.

Several exemplary embodiments will be explained below on the basis of the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 7a is a schematic view showing a ninth embodiment of a liquid evaporator according to the invention; and FIG. 7b is a schematic view showing a tenth embodiment of a liquid evaporator according to the invention.

DESCRIPTION OF THE PREFERRED EMBODIMENTS

Figure 1:
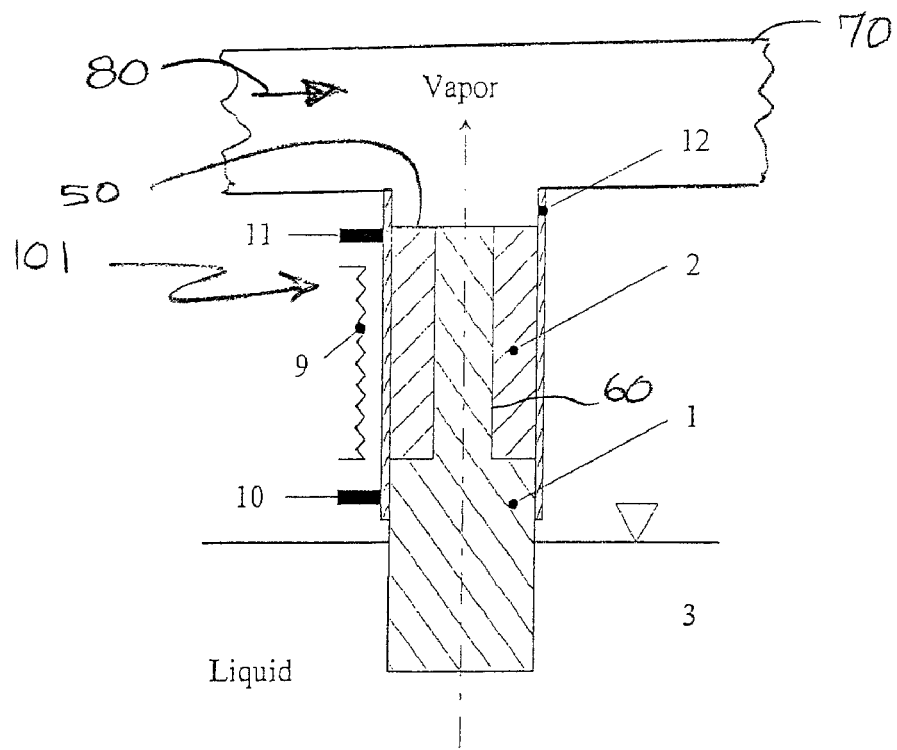
FIG. 1 is a schematic view showing a first embodiment of a liquid evaporator according to the invention.

Referring to the drawings in particular, the invention comprises a liquid evaporator generally designated 101-110 in FIGS. 1-7a. The liquid evaporators 101-110 include a liquid reservoir 3 with a liquid to be evaporated, a heater 9 and an evaporator tube 12. The evaporator tube 12 has a first porous element 1 having a first porosity and with an area in contact with the liquid in the liquid reservoir 3. The evaporator tube 12 also has a second porous element 2 with an area present on an evaporator side 50 used to dispense the evaporated liquid. The tube 12 has an area outside the liquid reservoir heated by the heater 9 which is not directly in connection with the liquid. The first porous element 1 and the second porous element 2 are in contact in contact areas 60 with the first porous element forming a wick delivering liquid from the reservoir to the contact area. The mean pore size of the sintered metal or sintered ceramic (2) which is not directly in connection with the liquid is greater than about 40 μm (preferably in the range of 40 μm to 100 μm) and the mean pore size of the sintered glass or sintered ceramic element (1) which is in connection with the liquid is 10 μm to 40 μm in case of the evaporation of water and 1 μm to 40 μm in case of the evaporation of anesthetic. At the evaporator side 50 the liquid evaporator 101-110 is connected to a respirator or anesthetic device 70 with respiration flow 80. The area or areas of the liquid evaporator 101-110 that are in connection with the liquid are equipped with a gas-tight jacket or are inserted into the evaporator tube such that the liquid cannot escape from the evaporator tube to the outside against the direction of dispensing when a respiration pressure is present on the front side for dispensing the evaporated liquid.

In FIG. 1, the porous sintered glass or porous sintered ceramic element 1 has a porosity of, e.g., P16 (mean pore diameter 10 μm to 16 μm) and acts as a capillary wick. The porous sintered glass or porous sintered ceramic element 1 is in connection with the liquid reservoir 3. The heater 9 is located in the upper area of the evaporator tube 12 consisting of a Cr—Ni steel. The sintered glass or sintered ceramic element 1 is surrounded in the upper section by a porous sintered metal or a porous sintered ceramic 2. Two temperature sensors 10, 111 may be provided to regulate the heater 9.

Figure 2:
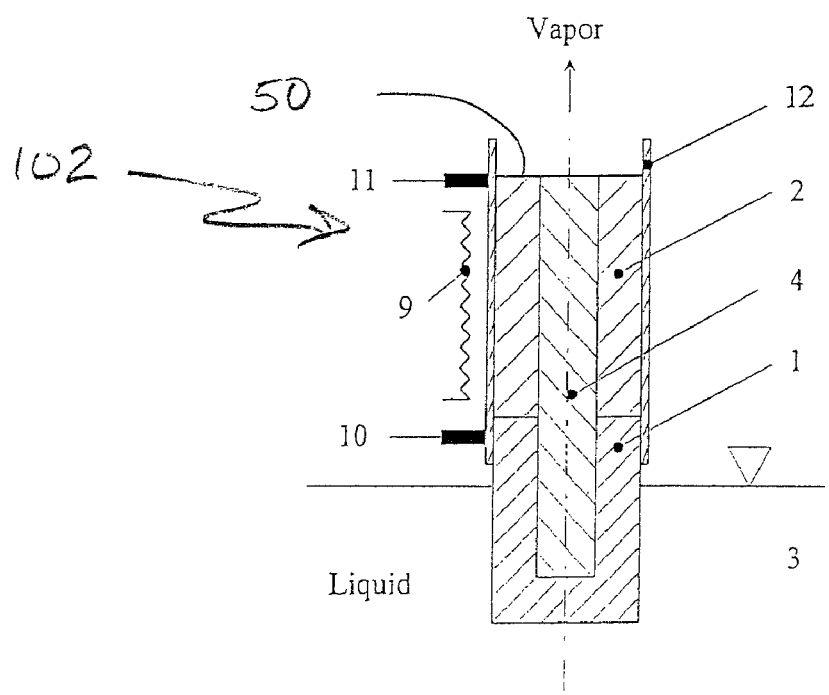
FIG. 2 is a schematic view showing a second embodiment of a liquid evaporator according to the invention.

According to FIG. 2, a relatively long, porous sintered ceramic element 4 with a porosity in the range of P16 to P100 is used, which is surrounded in the upper section from the outside by the porous sintered metal or porous sintered ceramic 2, which is heated by means of the heater 9 and is introduced into the evaporator tube 12 and in the lower section by the porous sintered glass or porous sintered ceramic element 1, with a porosity of, e.g., P16. Due to the use of the sintered glass or sintered ceramic element 1 having relatively poor thermal conduction, the heat losses to the liquid side in the liquid reservoir 3 are reduced.

Figure 3:
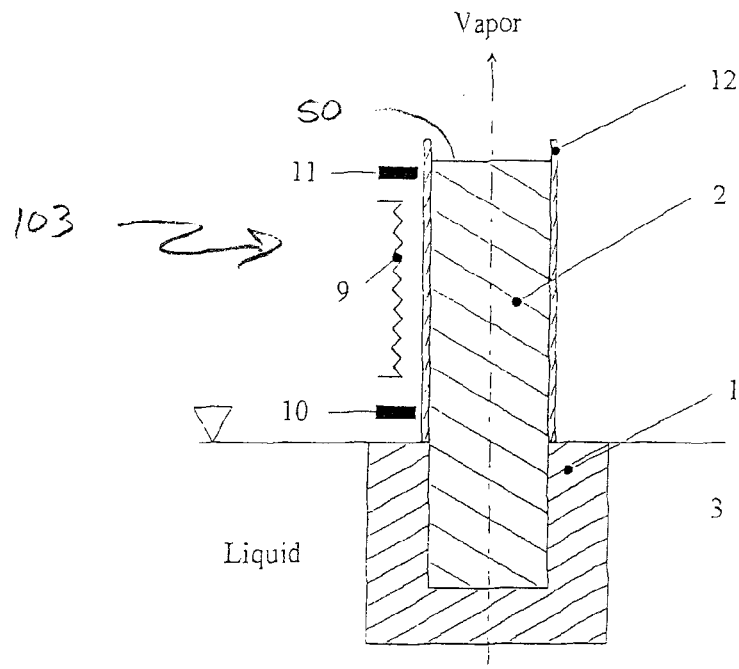
FIG. 3 is a schematic view showing a third embodiment of a liquid evaporator according to the invention.

An element formed as a "pot wick" from a porous sintered glass or porous sintered ceramic element 1 with a porosity of, e.g., P16 is used in FIG. 3, and it is introduced or immersed directly into the liquid to be evaporated in the liquid reservoir 3. The porous sintered metal or porous sintered ceramic 2, which is heated by means of the heater 9 and is introduced into the evaporator tube 12, is in contact with the inside of 1. As a result, the capillary forces are supported by the liquid pressure present on the outside. In addition, the effective capillary length for the flow is reduced.

Figure 4A:
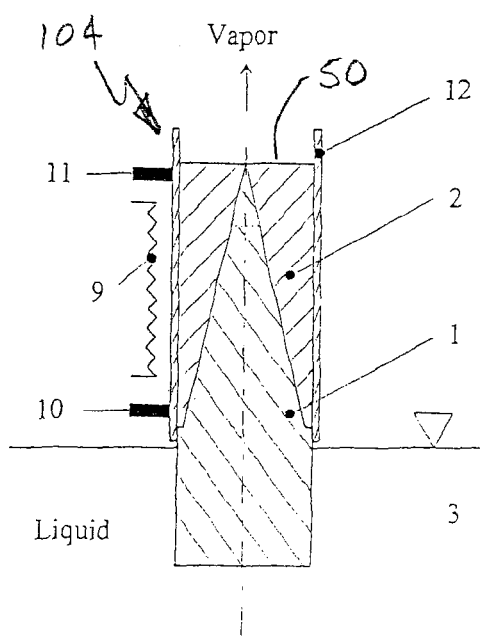
FIG. 4a is a schematic view showing a fourth embodiment of a liquid evaporator according to the invention.
Figure 4B:
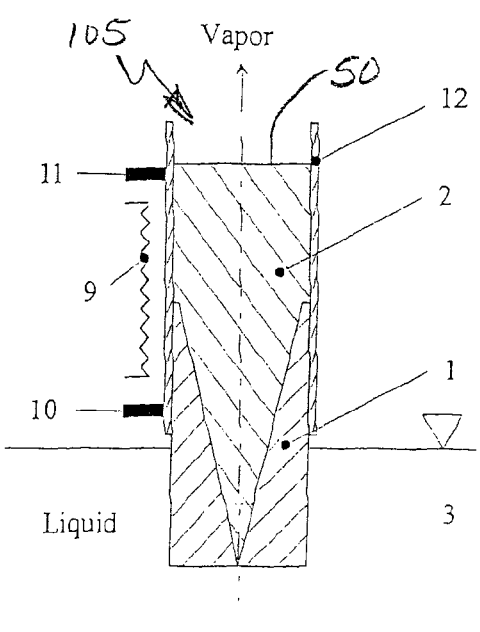
FIG. 4b is a schematic view showing a fifth embodiment of a liquid evaporator according to the invention.

According to FIGS. 4a and 4b, the evaporation capacity is increased by a continuous change in the cross section of the section of the liquid evaporator, which section acts as a capillary wick. The porous sintered glass or porous sintered ceramic element 1, with a porosity of, e.g., P16, is formed in the upper section in the form of a convex or concave circular cone or truncated circular cone on a cylindrical section. The element 1 is directly in contact with the porous sintered metal or porous sintered ceramic 2, which is heated by means of the heater 9 and is introduced into the metallic evaporator tube 12, and immerses into the liquid to be delivered, which is located in the liquid reservoir 3.

Figure 5A:
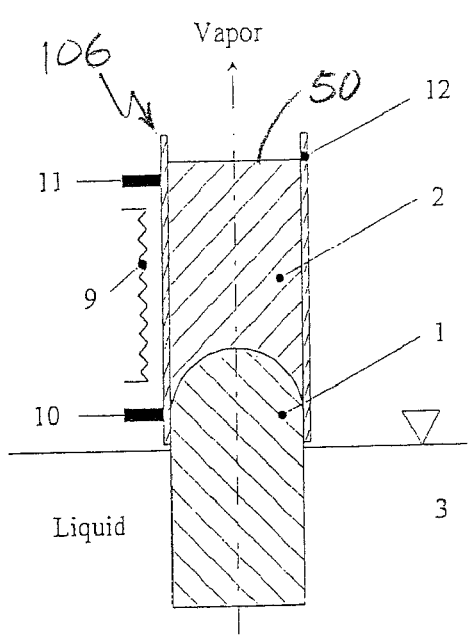
FIG. 5a is a schematic view showing a sixth embodiment of a liquid evaporator according to the invention.
Figure 5B:
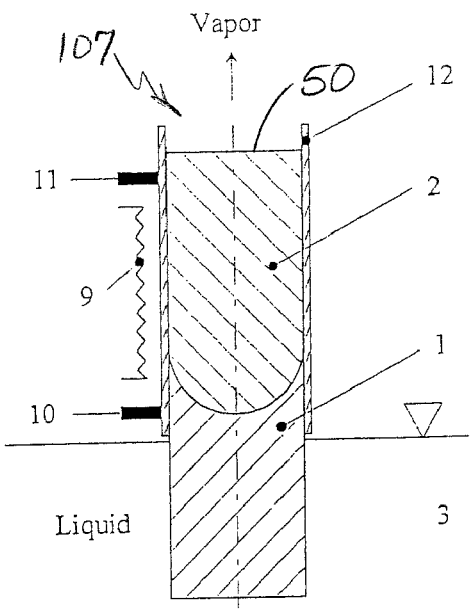
FIG. 5b is a schematic view showing a seventh embodiment of a liquid evaporator according to the invention.

According to FIGS. 5a and 5b, the interface between the elements 1 and 2 is in the form of a hemisphere, a spherical segment, a rotation paraboloid or a truncated rotation paraboloid. It is essential in any case that the three-dimensional contact area between the element 1 acting as the capillary wick and element 2 is increased continuously, so that the velocity of flow of the liquid and the dispensing of the liquid into the section with the evaporator tube 12 is approximately constant and the evaporation capacity is increased.

Figure 6:
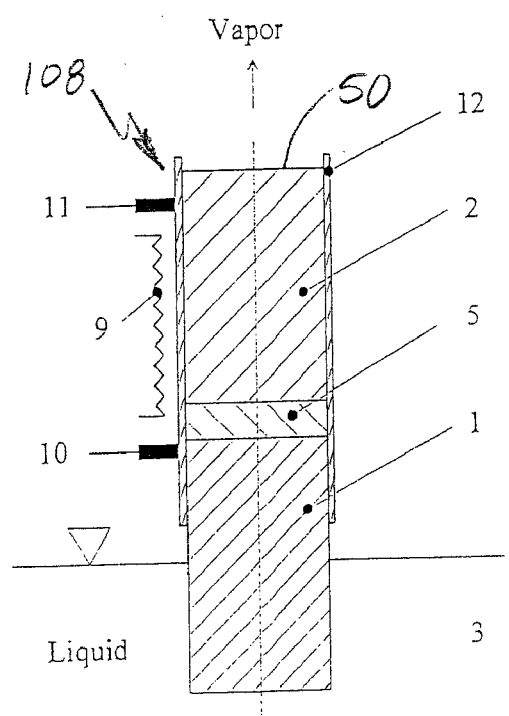
FIG. 6 is a schematic view showing an eighth embodiment of a liquid evaporator embodiment of a liquid evaporator according to the invention.

According to the embodiment shown in FIG. 6, the fine porous section of the capillary wick has only a small three-dimensional extension and offers only a low flow resistance to the liquid transport: A wick section of a sandwich-like structure is composed of two porous sintered glass or porous sintered ceramic elements, the upper element 5 being in contact with the porous sintered metal or porous sintered ceramic 2, which is heated by means of the heater 9 and is introduced into the evaporator tube 12 and has a relatively fine porosity, for example, P16 with a mean pore size of 10 μm to 16 μm. The lower porous sintered glass or porous sintered ceramic 1 is in contact with the liquid to be delivered and evaporated in the liquid reservoir 3 and has a relatively coarse pore structure, for example, P100 with a mean pore size of 40 μm to 100 μm. The gas side is separated from the liquid side by means of the upper element 5, i.e., independence from the back pressure becomes established, because the capillary pressure markedly exceeds the respiration pressure. A sufficient liquid supply is ensured by the lower element 1 with a relatively low flow resistance.

FIGS. 7a and 7b show a liquid evaporator with improved handling and installation properties with the sealing of the section acting as the capillary wick toward the environment. The gap between the evaporator tube 12 and the element 1 is sealed by means of a construction element 7, while a smooth jacket surface is formed. The lower element 1, with a porosity of, e.g., P16, has on the outside such a gas-tight jacket 6 or 8, for example, by melting on the sintered material or by applying a gas-sealing coating, for example, in the form of a ceramic adhesive.

The heater 9 is preferably arranged in all embodiments such that its principal action is located in the area of the porous sintered metal or porous sintered ceramic 2 up into the area of the three-dimensional contact area to the porous sintered glass or porous sintered ceramic element 1. Heating of the lower area, i.e., of the porous sintered glass or porous sintered ceramic element 1, shall be possibly avoided in order to prevent heating of the liquid to be delivered and thus not to compromise the wick action.

The embodiments according to FIGS. 1 through 6 can likewise be provided with a gas-tight jacket 6 according to FIGS. 7a and 7b.

If the external diameter of the section acting as a capillary wick is, for example, 10 mm, the embodiments according to FIGS. 3; 4a, 4b; 5a, 5b are preferred for the same use as anesthetic or water evaporators in case of high evaporation capacity, and the version according to FIG. 1 is preferred in case of low and medium evaporation capacity.

While specific embodiments of the invention have been shown and described in detail to illustrate the application of the principles of the invention, it will be understood that the invention may be embodied otherwise without departing from such principles.

What is claimed is:

1. A liquid evaporator comprising:
   a liquid reservoir with a liquid to be evaporated;
   an evaporator tube;
   a heater for heating the evaporator tube, the evaporator tube having adjacent areas consisting of materials of different porosities, including one or more areas with one or more porous sintered glass or porous sintered ceramic elements, which said areas are in connection with the liquid in the liquid reservoir and are present on one front side of the liquid evaporator wherein the other front side is used to dispense the evaporated liquid, and an area of the evaporator tube outside the liquid reservoir, which said area is heated by means of the heater provided with a porous sintered metal or said porous sintered ceramic, which is not directly in connection with the liquid with at least two different cross section distributions of the materials having different porosities present in the longitudinal direction of the liquid evaporator, and the areas in the liquid evaporator are adjacently in connection by means of three-dimensionally shaped contact areas.

2. A liquid evaporator in accordance with claim 1, wherein the area or areas of the liquid evaporator that is/are in connection with the liquid is/are equipped with a gas-tight jacket or is/are inserted into the evaporator tube such that the liquid cannot escape to the outside against the direction of dispensing from the evaporator tube when a respiration pressure is present on the front side to dispense the evaporated liquid.

3. A liquid evaporator in accordance with claim 1, wherein the mean pore size of the sintered metal or sintered ceramic which is not directly in connection with the liquid is greater than about 40 µm and the mean pore size of the sintered glass or sintered ceramic element which is in connection with the liquid is 10 µm to 40 µm in case of the evaporation of water and 1 µm to 40 µm in case of the evaporation of anesthetic.

4. A liquid evaporator in accordance with claim 1, wherein the sintered metal consists of a stainless steel or an alloy containing copper or a chrome-nickel alloy.

5. A liquid evaporator in accordance with claim 1, wherein the liquid evaporator is provided with a first temperature sensor for regulating the heating capacity of said heater downstream of the section heated by means of the heater.

6. A liquid evaporator in accordance with claim 5, wherein the liquid evaporator is provided with a second temperature sensor upstream of the section heated with the heater for regulating the heating capacity of the heater so that overheating of the section upstream of the heated section is prevented.

7. A liquid evaporator in accordance with claim 1, wherein the front side for dispensing the evaporated liquid is connected to an evaporator chamber in the breathing gas flow of a patient, especially as part of an anesthesia apparatus or a respirator.

8. A liquid evaporator in accordance with claim 1, wherein the liquid is one of an anesthetic, water, a solution or a solution containing a drug.

9. A liquid evaporator in accordance with claim 1, wherein the sintered ceramic consists of $Al_2O_3$.

10. A liquid evaporator in accordance with claim 1, wherein the three-dimensionally shaped contact area is designed in the form of a cone, a sphere or a rotation paraboloid, especially with a convex or concave shape.

11. A liquid evaporator in accordance with claim 1, wherein the area or areas of the liquid evaporator that is/are in connection with the liquid in the liquid reservoir is/are inserted into the evaporator tube such that a gap formed between the evaporator tube and the at least one sintered glass or sintered ceramic element is at most 10 times the mean pore size of the element, so that the liquid cannot escape to the outside against the direction of dispensing from the evaporator tube and also no leakage of gas can thus occur when a respiration pressure is present on the front side for dispensing the evaporated liquid.

12. A liquid evaporator comprising:
   a liquid reservoir with a liquid to be evaporated;
   a heater;
   an evaporator tube which is heated by said heater, said evaporator tube having adjacent areas comprising materials having different porosities, wherein one or more of said areas including one or more porous sintered glass or porous sintered ceramic elements with areas in connection with the liquid in the liquid reservoir being present on one front side of the liquid evaporator and the other front side being used to dispense the evaporated liquid, and including an area of the evaporator tube outside the liquid reservoir heated by means of the heater and equipped with a porous sintered metal or said porous sintered ceramic which is not directly in connection with the liquids wherein at least two different cross section distributions of the materials having different porosities are present in the longitudinal direction of the liquid evaporator, and the area or areas of the liquid evaporator that are in connection with the liquid are equipped with a gas-tight jacket or are inserted into the evaporator tube such that the liquid cannot escape from the evaporator tube to the outside against the direction of dispensing when a respiration pressure is present on the front side for dispensing the evaporated liquid.

13. A liquid evaporator in accordance with claim 12, wherein the areas in the liquid evaporator are adjacently in connection by means of three-dimensionally shaped contact areas.

14. A liquid evaporator in accordance with claim 12, wherein the mean pore size of the sintered metal or sintered ceramic which is not directly in connection with the liquid is greater than about 40 µm and the mean pore size of the sintered glass or sintered ceramic element which is in connection with the liquid is 10 μm to 40 μm in case of the evaporation of water and 1 μm to 40 μm in case of the evaporation of anesthetic.

15. A liquid evaporator in accordance with claim 12, wherein the sintered metal comprises a stainless steel or an alloy containing copper or a chrome-nickel alloy.

16. A liquid evaporator in accordance with claim 12, wherein the liquid evaporator is provided with a first temperature sensor for regulating the heating capacity of said heater downstream of the section heated by means of the heater.

17. A liquid evaporator in accordance with claim 16, wherein the liquid evaporator is provided with a second temperature sensor upstream of the section heated with the heater for regulating the heating capacity of the heater so that overheating of the section upstream of the heated section is prevented.

18. A liquid evaporator in accordance with claim 12, wherein the front side for dispensing the evaporated liquid is connected to an evaporator chamber in the breathing gas flow of a patient, especially as part of an anesthesia apparatus or a respirator.

19. A liquid evaporator in accordance with claim 12, wherein the liquid is one of an anesthetic, water, a solution or a solution containing a drug.

20. A liquid evaporator in accordance with claim 12, wherein the sintered ceramic consists of $Al_2O_3$.

21. A liquid evaporator in accordance with claim 12, wherein the three-dimensionally shaped contact area is designed in the form of a cone, a sphere or a rotation paraboloid, especially with a convex or concave shape.

22. A liquid evaporator in accordance with claim 12, wherein the area or areas of the liquid evaporator that is/are in connection with the liquid in the liquid reservoir is/are inserted into the evaporator tube such that a gap formed between the evaporator tube and the at least one sintered glass or sintered ceramic element is at most 10 times the mean pore size of the element, so that the liquid cannot escape to the outside against the direction of dispensing from the evaporator tube and also no leakage of gas can thus occur when a respiration pressure is present on the front side for dispensing the evaporated liquid.

23. A liquid evaporator comprising:

a liquid reservoir with a liquid to be evaporated;

a heater;

an evaporator tube with a first porous element having a first porosity and with an area in contact with the liquid in the liquid reservoir and a second porous element having a second porosity and with an area present on an evaporator side used to dispense the evaporated liquid, said evaporator tube having an area heated by the heater which is not directly in connection with the liquid, said first porous element and said second porous element being in contact with each other in a contact area with said first porous element forming a wick delivering liquid from the reservoir to said contact area, wherein the area or areas of the liquid evaporator that is/are in connection with the liquid includes a sealed wick connection including a gas-tight jacket or insertion of the evaporator tube into the liquid such that the liquid cannot escape to the outside against the direction of dispensing from the evaporator tube when a respiration pressure is present on the evaporator side to dispense the evaporated liquid.

24. A liquid evaporator in accordance with claim 23, wherein the first porous element and second porous element are adjacently in connection by means of three-dimensionally shaped contact areas.

* * * * *